United States Patent [19]

Alcock

[11] Patent Number: 5,542,444

[45] Date of Patent: Aug. 6, 1996

[54] VALVE AND METHOD OF USING

[75] Inventor: Alan J. Alcock, Mundelein, Ill.

[73] Assignee: Abbott Laboratories, Abbott Park, Ill.

[21] Appl. No.: 401,582

[22] Filed: Mar. 9, 1995

Related U.S. Application Data

[63] Continuation-in-part of Ser. No. 334,902, Nov. 7, 1994.

[51] Int. Cl.$^6$ ................................................ F16K 31/126
[52] U.S. Cl. ............................... 137/1; 251/61.1; 251/331
[58] Field of Search .................................. 251/61.1, 331; 137/1

[56] References Cited

U.S. PATENT DOCUMENTS

| | | | |
|---|---|---|---|
| 2,842,400 | 7/1958 | Booth et al. | 251/331 X |
| 3,083,943 | 4/1963 | Stewart et al. | 251/61.1 |
| 3,286,977 | 11/1966 | Miottel | 251/331 X |
| 3,477,693 | 11/1969 | Benzanis | 251/251 |
| 3,600,953 | 8/1971 | Isreeli et al. | 73/423 A |
| 3,740,019 | 6/1973 | Kessell et al. | 251/331 X |
| 3,749,353 | 7/1973 | Pauliukonis | 251/61.1 |
| 3,934,611 | 1/1976 | Gachot et al. | 137/603 |
| 3,951,167 | 4/1976 | Howell et al. | 251/331 X |
| 4,070,004 | 1/1978 | Friswell | 251/331 |
| 4,119,120 | 10/1978 | Mehaffy et al. | 137/885 |
| 4,168,724 | 9/1979 | Graffunder et al. | 137/606 |
| 4,259,291 | 3/1981 | Smythe | 422/82 |
| 4,304,257 | 12/1981 | Webster | 137/559 |
| 4,307,257 | 12/1981 | Webster | 137/559 |
| 4,353,243 | 10/1982 | Martin | 73/23.1 |
| 4,399,362 | 8/1983 | Cormier et al. | 250/430 |
| 4,479,762 | 10/1984 | Bilstad et al. | 417/395 |
| 4,601,881 | 7/1986 | Webster | 422/67 |

(List continued on next page.)

FOREIGN PATENT DOCUMENTS

| | | |
|---|---|---|
| 420296 | 3/1991 | European Pat. Off. . |
| 562694 | 9/1993 | European Pat. Off. . |

OTHER PUBLICATIONS

Branebjerg, Jens and Peter Gravesen. "A New Electrostatic Actuator providing improved Stroke length and Force". IEEE Micro Electro Mechanical Systems '92, Travelmünde, Germany, Feb. 4–7, 1992, pp. 6–11.

Huff, Michael A. et al. "A Pressure–Balanced Electrostatically–Actuated Microvalve". IEEE Solid Sensor and Actuator Workshop, Technical Digest, Hilton Head, S.C., Jun. 4–7, 1990, pp. 123–127.

Huff, Michael A. et al. "A Pressure Switch Utilizing Plastic Deformation of Silicon". IEEE 91CH2817–5/91/0000–0177, 1991, pp. 177–180.

Jensen, D. F. "Pneumatic Digital Control of a Synchronous Device". *Fluidics Quarterly* vol. 1 No. 1, 1967, pp. 27–37.

Manning, J. R. "Fluidic Control Devices and Systems". *Fluidics Quarterly*, ca. 1970.

Ohnstein, T. et al. "Micromachined Silicon Microvalve". IEEE Micro Electro Mechanical Systems, Napa Valley, CA, Feb. 11–14, 1990, pp. 95–98.

Ruzicka and Hansen, *Chemical Analysis Vol. 62 Flow Injection Analysis*, 2d Ed., John Riley & Sons, New York (1988), ISBN 0–471–81355–9.

*Primary Examiner*—Gerald A. Michalsky
*Attorney, Agent, or Firm*—Mark C. Bach

[57] ABSTRACT

Embodiments described herein relate to a valve and a method of use. In one embodiment, a first element is operatively and removably positioned with respect to a first fluid conveying conduit and a second fluid conveying conduit. The first element is movable between a first position where no fluid communicates between the first fluid conveying conduit and the second fluid conveying conduit and a second position where fluid communicates between the first fluid conveying conduit and the second fluid conveying conduit. A second element is operatively and removably engagable with the first element for maintaining operative position of the first element with respect to the first fluid conveying conduit and the second fluid conveying conduit. A third element is operatively and removably engagable with the second element for maintaining engagement between the first element and the second element.

2 Claims, 2 Drawing Sheets

U.S. PATENT DOCUMENTS

| | | | |
|---|---|---|---|
| 4,773,446 | 9/1988 | Farnsworth | 251/61.1 X |
| 4,848,722 | 7/1989 | Webster | 251/61.1 |
| 4,852,851 | 8/1989 | Webster | 251/61.1 |
| 4,853,336 | 8/1989 | Saros et al. | 436/53 |
| 4,858,883 | 8/1989 | Webster | 251/61.1 |
| 4,867,201 | 9/1989 | Carten | 251/331 X |
| 5,045,473 | 9/1991 | Cassaday et al. | 436/53 |
| 5,149,658 | 9/1992 | Cassaday et al. | 436/53 |
| 5,180,138 | 1/1993 | Moldenhauer | 251/45 X |
| 5,265,843 | 11/1993 | Kleinhappl | 251/331 X |
| 5,391,353 | 2/1995 | Graffunder | 422/103 |

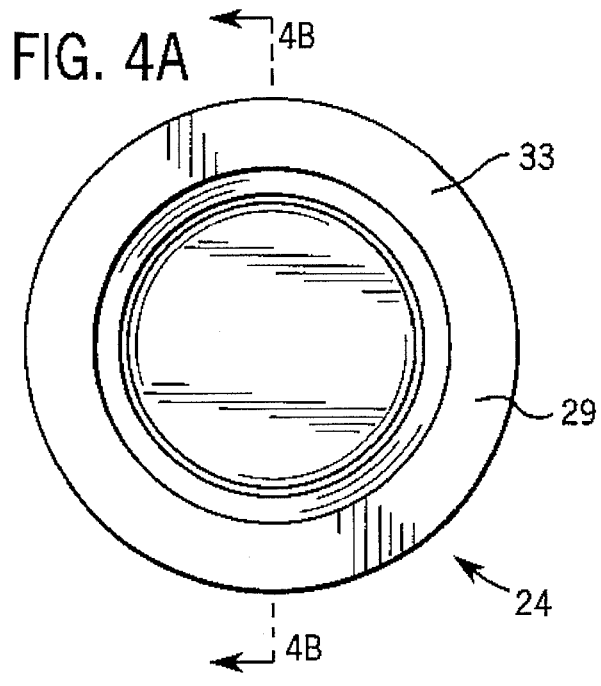
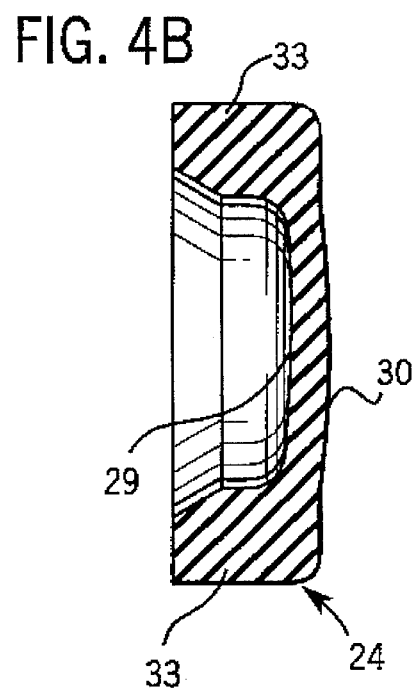
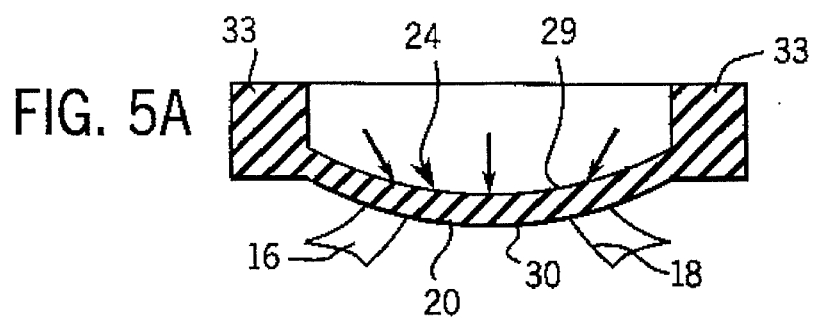
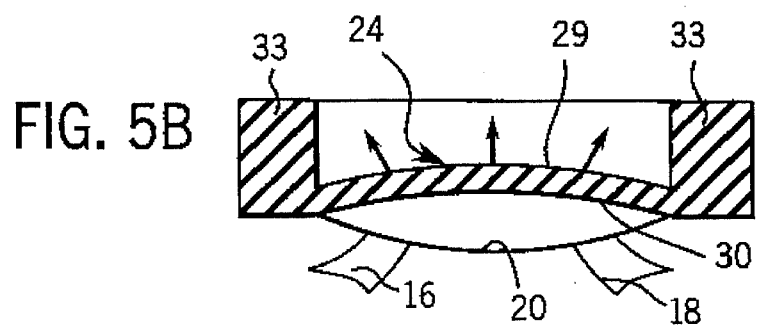

VALVE AND METHOD OF USING

REFERENCE TO RELATED APPLICATION

This application is a continuation-in-part application of copending U.S. patent application Ser. No. 08/334,902, titled METHOD AND APPARATUS FOR METERING A FLUID, filed on Nov. 7, 1994, and which is assigned to the assignee of the present invention. The disclosure of that patent application is incorporated herein in its entirety.

BACKGROUND OF THE INVENTION

Embodiments described herein relate to a valve and a method for using a valve.

One type of valve currently available, such as that disclosed in the above-referenced patent application, consists of a flexible member sandwiched between two rigid members. Fluid conveying conduits and valve bodies are formed, e.g. machined, etc., on at least one of the rigid members. The flexible member is placed between the two rigid members. The rigid members are held together by a fastener, such as a screw and the like, so that the flexible member is clamped between the two rigid members. In some constructions, an adhesive may be used to secure the flexible member between the two rigid members.

Over time, it may be desirable to repair or to replace the flexible member. To access the flexible member, it is necessary to remove the fastener. As a given valve may be associated with a larger fluid circuit, a number of fasteners may have to be removed. If an adhesive were used, removal of the flexible member may be complicated.

Because often one flexible member is used for multiple valves, fluid, the flow of which is controlled by the valves, may flow along the flexible member thereby possibly reducing the effectiveness of the valves. Use of only one flexible member may reduce the number of fluids that can be controlled by a given set of valves because the material comprising the flexible member should be chemically compatible with the fluids.

Given these considerations, it is desirable to provide an improved valve construction and method of using the valve.

SUMMARY OF THE INVENTION

Embodiments described herein relate to a valve and a method of use. According to one embodiment, a first element is operatively and removably positioned with respect to a first fluid conveying conduit and a second fluid conveying conduit. The first element is movable between a first position where no fluid communicates between the first fluid conveying conduit and the second fluid conveying conduit and a second position where fluid communicates between the first fluid conveying conduit and the second fluid conveying conduit. A second element is operatively and removably engagable with the first element for maintaining operative position of the first element with respect to the first fluid conveying conduit and the second fluid conveying conduit. A third element is operatively and removably engagable with the second element for maintaining engagement between the first element and the second element.

In another embodiment, a method of using a valve comprises inserting a first element into an aperture. The first element moves between a first position where fluid communicates between a first fluid conveying conduit and a second fluid conveying conduit and a second position where fluid does not communicate between the first fluid conveying conduit and the second fluid conveying conduit. A second element is inserted into the aperture. The first element operatively contacts the second element such that the first element is retained in operative position with respect to the first fluid conveying conduit and the second fluid conveying conduit. The first element moves into the first position. The first element moves into the second position. The second element is removed from the aperture. The first element is removed from the aperture.

An additional embodiment provides a valve having a first element movable between a first position where there is no fluid communication between a first fluid conveying conduit and a second fluid conveying conduit and a second position where fluid communicates between the first fluid conveying conduit and the second fluid conveying conduit. A second element operatively positions the first element with respect to the first fluid conveying conduit and the second fluid conveying conduit such that the first element determines fluid communication between the first fluid conveying conduit and the second fluid conveying conduit. The second element is removable for accessing the first element.

BRIEF DESCRIPTION OF THE DRAWINGS

FIG. 4A is an elevational view of another element of the valve of FIG. 1;

FIG. 4B is a sectional view, taken along line 4B—4B of FIG. 4A;

FIG. 5A is a partially sectioned view of a portion of the valve of FIG. 1 showing the valve in a first position; and FIG. 5B is a view similar to that of FIG. 5B showing the valve in a second position.

DETAILED DESCRIPTION OF PREFERRED EMBODIMENTS

For the sake of clarity of understanding, specific embodiments of the invention are discussed in detail. However, it is to be remembered that other embodiments are also possible. Elements of one embodiment may be combined in suitable manner with elements of another embodiment. For instance, steps of one method may be combined with steps of another method to arrive at yet other methods. The embodiments may be constructed from any appropriate materials and may be employed in any desirable structure, such as an analytical instrument and the like, with any desirable fluid. It is to be recognized that the embodiments may be operated in any desirable fashion, such as by fluids, i.e. pressure, electrostatics, electromagnetics and/or mechanics.

Figure 1:
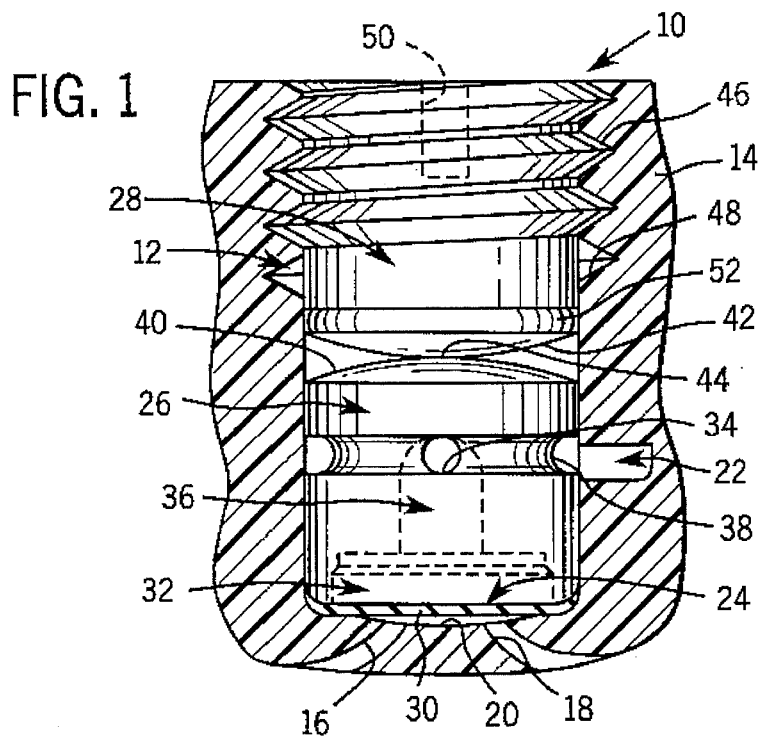
FIG. 1 is a partially sectioned view of a valve described in detail herein.

FIG. 1 illustrates a particular embodiment of a valve 10. The valve 10 is disposed within an aperture 12 in a body 14. The body 14 includes a first fluid conveying conduit 16 and a second fluid conveying conduit 18 which fluidly communicate along a surface 20. In one embodiment, the valve 10 may be a flow through valve and the first fluid conveying conduit 16 and the second fluid conveying conduit 18 may be portions of the same fluid conveying conduit. Such a construction may be substantially similar to the constructions disclosed in the above-referenced patent application. In an exemplary embodiment, the body 14 is made from a suitable polymeric material. In a specific embodiment, the aperture 12, as well as other structures on the body 14, is molded or is machined in the body 14 which is made of a plastic material such as acrylic and the like.

The valve 10 is movable between a first position (FIG. 5A) where there is no fluid communication between the first fluid conveying conduit 16 and the second fluid conveying conduit 18, viz. the first fluid conveying conduit 16 is substantially fluidly isolated from the second fluid conveying conduit 18, and a second position where the first fluid conveying conduit 16 fluidly communicates with the second fluid conveying conduit 18. In the illustrated embodiment, the body 14 also includes a third fluid conveying conduit 22 for providing a fluid or pressure to the valve 10 for moving the valve 10 between the first position and the second position. Accordingly, the third conduit 22 may be connected, possibly through a valve, to a source or sources (not shown) of fluid under desired pressures.

The illustrated embodiment of the valve 10 comprises a first element 24, a second element 26 and a third element 28. Although the elements 34, 26 and 28 are shown as separate pieces, in other embodiments, two or more of the elements 24, 26 and 25 may be combined, i.e. integrated, as a single element. For instance, the first element 24 may be joined with the second element 26, such as by ultrasonic or RF techniques and the like. Thus, in some embodiments, all of the elements 24, 26 and 28, or any subcombination of all of the elements 24, 26, and 28, such as elements 26 and 28, may be provided as a single piece. All of the elements 24, 26 and 28 are constructed to fit substantially within the aperture 12 in the body 14.

The first element 24, illustrated in detail in FIGS. 4A and 4B, has a configuration which may complement the configuration of the surface 20. In some embodiments, the first element 24 is substantially disk-shaped. In other embodiments, the surface 20 is substantially planar and, in still others, the first element 24 is domed or radiused. In yet further embodiments, the first element 24 may include a structure, such as a groove and the like, thereby enabling the associated valve 10 to perform as a fluid flow restrictor. Other employments, i.e. osmosis applications, are possible dependent upon construction of the first element 24.

The first element 24 determines whether the valve 10 is in the first position or in the second position. Accordingly, the first element 24 flexes between the position of FIG. 5A and the position of FIG. 5B under the influence of the pressure of the fluid present in the third conduit 22. In other embodiments, the first element 24 flexes dependent upon a pressure, such as an initial pressure, and/or a vacuum applied to the first element 24. To facilitate flexing, in one embodiment the first element 24 is made of an elastomer. In a specific embodiment, the first element 24 is made from an elastic solid material, such as ethylene propylene diamine monomer (EPDM) and the like.

Movement of the valve 10, or flexing of the first element 24 depends upon fluid pressure present in the third conduit 22 being exposed to a first or pressure side 29 of the first element 24. When the valve 10 is in the first position (FIG. 5A), the first element 24 flexes such that a second or contacting side 30 of the first element 24 engages the surface 20 of the aperture 12. The engagement between the contacting side 30 of the first element 24 and the surface 20 is sufficient to limit or to eliminate fluid communication between the first fluid conveying conduit 16 and the second fluid conveying conduit 18. When the valve 10 is in the second position (FIG. 5B), the contacting side 30 of the first element 24 is offset from the surface 20 of the aperture 12 sufficiently to allow or to restrict fluid communication between the first fluid conveying conduit 16 and the second fluid conveying conduit 18.

The magnitude of the engagement and the offset is dependent upon a number of factors, such as the fluid pressure present in the third conduit 22, finish on mating or engaging components, materials used, associated fluid pressures, etc. For example, if it were desired to have the valve 10 in the first position, then the pressure exposed to the first side 29 of the first element 24 would be approximately larger than any pressure present in either the first fluid conveying conduit 16 or the second fluid conveying conduit 18. If it were desired to have the valve 10 in the second position, then the pressure exposed to the first side 29 of the first element 24 would be approximately less than the lowest pressure present in either the first fluid conveying conduit 16 or the second fluid conveying conduit 18.

In one embodiment, to maintain the valve 10 in the second position, the pressure exposed to the first side 29 of the first element 24 is approximately less than the pressures present in the first fluid conveying conduit 16 and the second fluid conveying conduit 18. In this way, the magnitude of applied pressure is chosen to operate the valve 10 in a desired fashion. In an exemplary embodiment, when the valve 10 is in the first position, a pressure of about 6 or 7 psig is exposed to the first side 29 of the first element 24', and when the valve 10 is in the second position, the pressure exposed to the first side 29 of the first element 24 is about 16 inches Hg. The fluid pressures present in both the first fluid conveying conduit 16 and the second fluid conveying conduit 18 are about 5 psig.

The second element 26 keeps the first element 24 adjacent or in operative position with respect to the surface 20, the first fluid conveying conduit 16 and the second fluid conveying conduit 18. The second element 26 is configured such that the second element 26 is disposable substantially within the aperture 12 in the body 14. The second element 26, in the illustrated embodiment, has a substantially cylindrical configuration. In an exemplary embodiment, the second element 26 is formed, i.e. machined, molded, etc., of a polymeric material, such as an acrylic and the like.

Figures 2A, 2B, 2C:
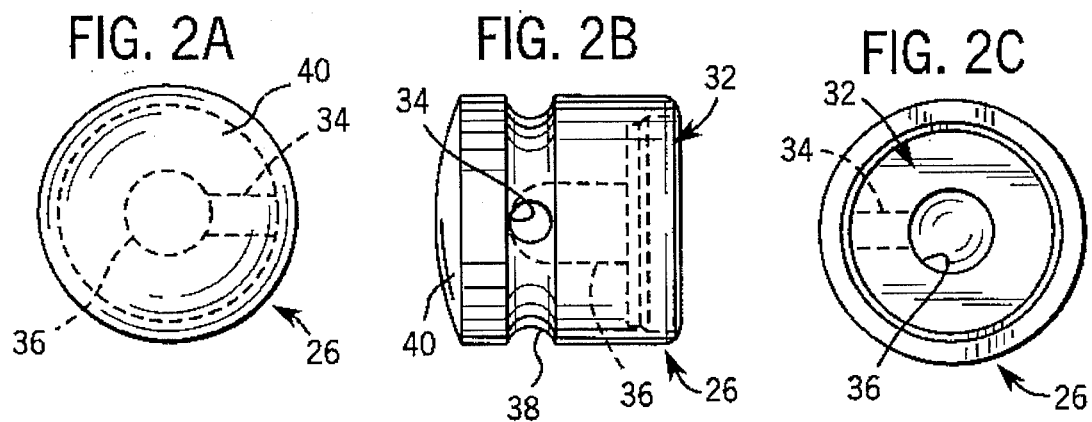
FIG. 2A is an elevational view of a side of an element of the valve of FIG. 1.
FIG. 2B is a side elevational view of the element of FIG. 2A.
FIG. 2C is an elevational view of a side of the element of FIG. 2A.

As shown more clearly in FIGS. 2A, 2B and 2C, in the illustrated embodiment, the second element 26 includes a structure 32, such as a recess, a counterbore and the like, which mates with the first element 24 to form a substantially fluid tight seal therebetween upon assembly. Specifically, the structure 32 on the second element 26 mates with a relatively enlarged portion 33 of the first element 24. Mating of the first element 24 and the second element 26 provided by the structure 32 and the portion 33 offers a substantially fluid tight fit between the first element 24 and the second element 26 when assembled. Thus, fluid pressure provided to the first element 24 through the second element 26 does not substantially leak thereby allowing the first element 24 to function as intended. Cooperation between the first element 24 and the second element 26 substantially fluidly isolates exposure of the first side 29 of the first element 24 to fluid pressure present within the third conduit 22.

In one particular embodiment, dimensions of the first element 24 and the second element 26 are predetermined to provide a desired, substantially fluid tight fit between the first element 24 and the second element 26 and between the surface 20 and the contacting side 30 of the first element 24. In this embodiment, when the first element 24 is assembled with the second element 26, i.e. the enlarged portion 33 of the first element 24 engages the structure 32 on the second element 26, the contacting side 30 of the first element 24 is offset from an adjacent end of the second element 26 by a predetermined distance, in one embodiment measuring about 0.008 inches.

When the valve 10 is assembled, the second element 26 approaches the surface 20 of the aperture 12 thereby compressing the first element 24 through a distance substantially equal to the predetermined distance mentioned above to form the substantially fluid tight seal. Additionally, engagement between the surface 20 of the aperture 12 and the second element 26 positively stops further axial advance of the second element 26 within the aperture 12. The positive stop provided by the engagement between the second element 26 and the surface 20 reduces the likelihood that a force of magnitude sufficient to compromise integrity of the valve 10 will be applied during assembly of the valve 10. Thus, in one embodiment, the positive stop reduces the likelihood that the third element 28 will be "over torqued" within the aperture 12 during assembly of the valve 10.

To convey fluid pressure to the first element 24, the second element 26 includes a substantially radial bore 34 and a substantially axial bore 36. An end of the substantially axial bore 36 opposite to the end thereof adjacent the substantially radial bore 34 is disposed adjacent the structure 32. The substantially radial bore 34 fluidly communicates with the substantially axial bore 36 to permit fluid communication between the third conduit 22 and the first side 29 of the first element 24. Specifically, fluid pressure introduced from the third conduit 22 to the substantially radial bore 34 is communicated to the substantially axial bore 36 and exposed to the first side 29 of the first element 24.

In one embodiment, to permit introduction of fluid pressure from the third conduit 22 to the substantially radial bore 34, an end of the substantially radial bore 34 opposite to the end thereof adjacent the substantially axial bore 36 fluidly communicates with a recess 38 on the second element 26. The recess 38 may be of any desired configuration that facilitates fluid communication between the third conduit 22 and the substantially radial conduit 34. For instance, the recess 38 may have a configuration which complements the corresponding configuration of relevant portions of the aperture 12 in the body 14. In the illustrated embodiment, the recess 38 extends substantially circumferentially around an outer surface of the second element 26 so that specific alignment of the radial conduit 34 and the third conduit 22 is not necessary.

An end of the second element 26 opposite to the end thereof adjacent the structure 32 includes a member 40 which facilitates contact between the second element 26 and the third element 28. The third element 28 also includes a member 42 having a construction which complements the construction of the member 40. The particular construction of the members 40 and 42 chosen may be dependent upon the configuration of the aperture 12 in the body 14, the method of assembly of the valve 10, etc. In the illustrated embodiment, the members 40 and 42 are similarly radiused.

With this construction, the members 40 and 42 define a "point" 44 of contact between the second element 26 and the third element 28. The point 44 of contact between the second element 26 and the third element 28 reduces the likelihood that the second element 26 might move undesirably, e.g. rotate within the aperture 12 within the body 14, under the influence of a force applied to the second element 26 by the third element 28. Other constructions of the members 40 and 42 are also possible. In some embodiments, a friction-reducing substance, such as a grease, may be disposed between the members 40 and 42.

Figures 3A, 3B, 3C:
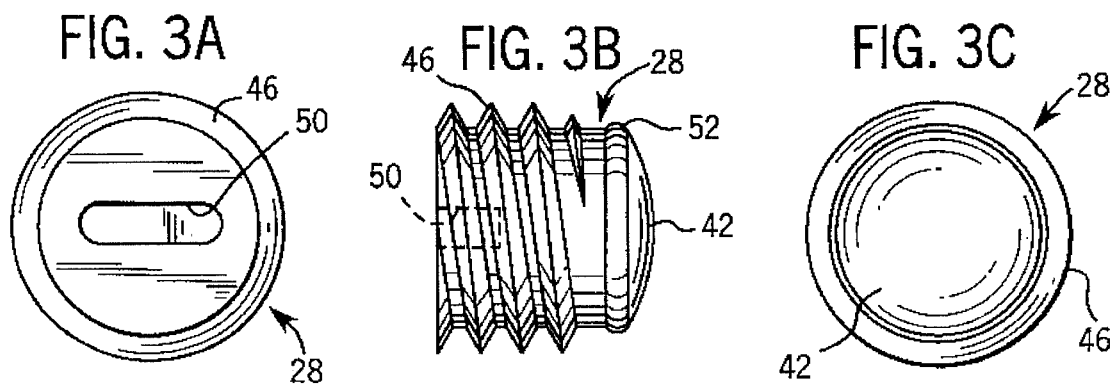
FIG. 3A is an elevational view of a side of another element of the valve of FIG. 1.
FIG. 3B is a side elevational view of the element of FIG. 3A.
FIG. 3C is an elevational view of a side of the element of FIG. 3A.

The third element 28 is shown in detail in FIGS. 3A, 3B and 3C. The third element 28 has a configuration which mates with the configuration of the aperture 12 in the body 14. In the illustrated embodiment, the third element 28 is substantially cylindrical. The third element 28 may be formed in any desired way from any desirable material, such as a polymer and the like. In an exemplary embodiment, the third element 28 is machined or molded from a polymer, such as acetal and the like.

The third element 28 includes a structure 46 for facilitating retention of the third element 28, and thus the second element 26 and the first element 24, operatively within the aperture 12. The structure 46 has a configuration which mates with a corresponding construction 48 on the aperture 12. In one embodiment, the structure 46 and the construction 48 comprise threads. Thus, the structure 46 on the third element 28 is rotatably or threadibly engaged with the construction 48 on the aperture 12. In another embodiment, the structure 46 and the construction 48 can be formed such that the third element 28 is retained within the aperture 12 in the body 14 by a press or interference fit. Any desired form of the structure 46 and the construction 48 is possible.

To aid in application and removal of the third element 28, and the valve 10 in general, to and from the aperture 12 in the body 14, the third element 28 includes a member 50 disposed on an end of the third element 28 opposite to the end thereof adjacent the member 42. The member 50 can take on a number of different forms such as those commonly used with fasteners. In the illustrated embodiment, the member 50 is a slot. In other embodiments, the member 50 may be constructed to facilitate force transfer during formation of a press or interference fit between the third element 28 and the aperture 12.

The third element 28 can include one or more seals 52, such as a rib, a ring, an O-ring and the like. The seal 52 reduces the probability of leaks from the valve 10. The seal 52 may be formed integrally with the third element 28 or may be provided as a separate piece. Additional seals may be provided at various locations with respect to the valve 10 to reduce leaks.

To provide greater understandings the following dimensions are given which are applicable to one embodiment of the valve 10. Other embodiments can have different dimensions. It is to be noted that these dimensions are provided as an example only.

The aperture 12 in the block 14 has an axial length of about 0.4 inches and a diameter substantially within the range of about 0.197 inches to about 0.199 inches.

The first element 24 has an outer diameter of about 0.155 inches. An inner diameter defined by the portion 33, which is substantially annular, measures about 0.095 inches. An inclined part of the portion 33 defines an angle of about 60 degrees. The portion 33 is about 0.046 inches high. The distance between the first side 29 and the second side 30 is about 0.011 inches.

The second element 26 has a height of about 0.18 inches and an outer diameter of about 0.195 inches. The radial bore 34 is disposed about 0.112 inches from an end of the second element 26 which is adjacent the first element 24. The radial bore 34 defines a diameter of about 0.031 inches. The recess 38 is about 0.035 inches wide and defines an outer diameter of about 0.16 inches. The axial bore 36 defines a diameter measuring about 0.063 inches. The member 40 is defined by a radius of about 0.25 inches.

The third element 28 has an axial length of about 0.208 inches and an outer diameter of about 0.192 inches. If present, the seal 52 defines an outer diameter of about 0.2 inches and has an axial length of about 0.020 inches. The member 50 extends about 0.06 inches axially from a head end of the third element 28 and has a width of about 0.039 inches and a length of about 0.09 inches. The structure 46 is ¼-28 UNF-2A threads with at least 3 full threads formed on the third element 28. The member 42 defines a radius of about 0.25 inches.

With the construction of the valve 10 being disclosed in detail, a method of using the valve 10 will now be discussed. The first element 24 may be applied to the second element 26 before or after the first element 24 is introduced into the aperture 12 in the block 14. If the first element 24 is applied to the second element 26 before the first element 24 is introduced into the aperture 12, then the first element 24 and the second element 26 are moved such that the portion 33 on the first element 24 engages the structure 32 on the second element 26. If the first element 24 is introduced into the aperture 12 prior to application of the first element 24 to the second element 26, then the first element 24 is introduced into the aperture 12 such that the second side 30 of the first element 24 opposes both the first fluid conveying conduit 16 and the second fluid conveying conduit 18. With the first element 24 in place within the aperture 12, the second element 26 is inserted into the aperture 12 such that the portion 33 engages the structure 32 as before.

In either instance, the first element 24 is joined with the second element 26 such that a pressure introduced into the axial bore 36 is exposed to the first side 29 of the first element 24. The recess 38 is fluidly aligned with the third conduit 22 so that pressure present in the third conduit 22 is introduced into the recess 38, the radial bore 34 and the axial bore 36. In some constructions, the configuration, e.g. out-of-round, of the second element 26 may align with a complementary configuration of a relevant portion of the aperture 12 such that the third conduit 22 fluidly communicates with the radial bore 34.

The third element 28 is introduced into the aperture 12 such that the member 42 opposes the member 40. The third element 28 is moved, i.e. rotated, axially translated, etc., such that the member 42 on the third element 28 contacts the member 40 on the second element 26. The point 44 of contact reduces force transfer from the third element 28 to the second element 26 to linearly or axially directed forces. The second element 26 does not rotate conjointly with the third element 28, thereby reducing the likelihood that the first element 24 will be moved from operative position with respect to the first fluid conveying conduit 16 and the second fluid conveying conduit 18.

The forces transferred from the third element 28 to the second element 26 cause the second element 26 to move axially within the aperture 12 thereby compressing the first element 24. Specifically, axial movement of the second element 26 within the aperture 12 compresses the portion 33 of the first element 24 thereby forming a substantially fluid tight seal between the first element 24 (the portion 33) and the second element 26 (the structure 32). The third element 28 is moved to generate the desired compression of the first element 24. This compression of the first element 24 is limited by the positive stop generated by contact between an end of the second element 26 and the surface 20 of the aperture 12. Engagement between the structure 46 and the construction 48 serves to maintain the position of the third element 28, and thereby the entire valve 10, with respect to the aperture 12. The valve 10 is ready for operation dependent upon application of an appropriate pressure to the third conduit 22.

It is to be noted that other constructions of the valve 10 may not require rotation of any element of the valve 10. For instance, the first and second elements 24 and 26, respectively, may be installed as described above. Then, the third element 28 can be axially introduced into the aperture 12 without rotational force. This method finds application where the third element 28 is retained within the aperture 12 by means of a press or interference fit.

To remove a valve 10, such as for repair, reuse or replacement, the order of the above-discussed steps are reversed.

To even further illustrate the valve 10, an example of operation of an embodiment of the valve 10 follows. It is assumed that the valve 10 is installed according to one of the methods described above.

The valve 10 is moved into the first position (FIG. 5A). To do this, a relatively increased pressure is fluidly connected with the third conduit 22. The relatively increased pressure occupies the third conduit 22, the recess 38, the radial bore 34 and the axial bore 36. The relatively increased pressure is exposed to the first side 29 of the first element 24. The relatively increased pressure flexes the first element 24 such that the second side 30 of the first element 24 contacts the surface 20 to reduce fluid communication between the first fluid conveying conduit 16 and the second fluid conveying conduit 18. The magnitude of the relatively increased pressure is predetermined such that the second side 30 of the first element 24 contacts the first fluid conveying conduit 16 and the second fluid conveying conduit 18 sufficiently such that there is little or no fluid communication between the first fluid conveying conduit 16 and the second fluid conveying conduit 18.

When it is desired to allow fluid communication between the first fluid conveying conduit 16 and the second fluid conveying conduit 18, the valve 10 is moved into the second position (FIG. 5B). To do this, a relatively reduced pressure is applied to the third conduit 22. The relatively reduced pressure occupies the third conduit 22, the recess 38, the radial bore 34 and the axial bore 36. The relatively reduced pressure is exposed to the first side 29 of the first element 24. The magnitude of the relatively reduced pressure is predetermined such that the second side 30 of the first element 24 moves away or is offset from the surface 20, the first fluid conveying conduit 16 and the second fluid conveying conduit 18. The first element 24 moves sufficiently away from the first fluid conveying conduit 16 and the second fluid conveying conduit 18 such that there is fluid communication between the first fluid conveying conduit 16 and the second fluid conveying conduit 18.

It is to be recognized that, by using the valve 10, a number of valves 10 may be provided in a given structure. However, because the valves 10 comprise independent first elements 24 operation, i.e. flexing of the first element 24, of one valve 10 does not effect operation of another valve 10. But, multiple valves 10 may be fluidly connected with the same third conduit 22 such that all such valves 10 fluidly connected with the same third conduit 22 operate in unison.

What is claimed is:

1. A method of using a valve in a body including a conduit for conveying operative fluid to the valve, the method comprising the steps of:

(a) inserting a diaphragm into an aperture in the body, the diaphragm being movable responsive to the operative fluid between a first position where fluid communicates between a first fluid conveying conduit and a second fluid conveying conduit in the body and a second position where fluid does not communicate between the first fluid conveying conduit and the second fluid conveying conduit in the body;

(b) inserting a second element into the aperture in the body, the second element including a bore for conveying operative fluid from the conduit in the body to the diaphragm;

(c) operatively contacting the diaphragm with the second element such that the diaphragm is retained in operative position with respect to the first fluid conveying conduit and the second fluid conveying conduit in the body;

(d) inserting a third element into the aperture in the body;

(e) operatively contacting the third element with the second element;

(f) compressing the diaphragm against the body under the influence of contact between the second element and the third element (g) moving the diaphragm into the first position with the operative fluid;

(h) moving the diaphragm into the second position with the operative fluid;

(i) removing the second element from the aperture in the body; and (j) removing the diaphragm from the aperture in the body.

2. A valve disposable within an aperture in a body having a conduit for conveying operative pressure to the valve, the valve determining fluid flow between a first fluid conveying conduit and a second fluid conveying conduit in the body, the valve comprising:

(a) a diaphragm operatively and removably positioned in the body with respect to the first fluid conveying conduit and the second fluid conveying conduit and movable responsive to the operative pressure between a first position where no fluid communicates between the first fluid conveying conduit and the second fluid conveying conduit in the body and a second position where fluid communicates between the first fluid conveying conduit and the second fluid conveying conduit in the body;

(b) a second element operatively and removably engagable with the diaphragm for maintaining operative position of the diaphragm with respect to the first fluid conveying conduit and the second fluid conveying conduit in the body, the second element including a bore for conveying operative pressure from the conduit in the body to the diaphragm;

(c) a third element operatively and removably engagable with the second element for maintaining engagement between the diaphragm and the second element; and (d) a seal disposed on the third element.

\* \* \* \* \*